United States Patent [19]

Prieto et al.

[11] Patent Number: 4,675,315
[45] Date of Patent: Jun. 23, 1987

[54] ANTIMICROBIAL SALT OF FOSFOMYCIN WITH IMIDAZOLE

[75] Inventors: Agustin P. Prieto; Arturo T. Higom; Maria d. P. C. Mata, all of Madrid, Spain

[73] Assignee: La Compania Espanola De La Penicilina Y Antibioticos, S.A., Madrid, Spain

[21] Appl. No.: 724,093

[22] Filed: Apr. 17, 1985

[30] Foreign Application Priority Data

Apr. 25, 1984 [GB] United Kingdom ................. 8410502

[51] Int. Cl.$^4$ .................. A61K 31/685; C07D 233/58
[52] U.S. Cl. ......................................... 514/76; 514/99; 548/335; 548/341; 548/342; 548/346
[58] Field of Search ............... 548/335, 341, 336, 342, 548/346; 514/397, 396, 76, 99

[56] References Cited

U.S. PATENT DOCUMENTS 2,750,379  6/1956  Hanslick et al. ................. 548/346 X
2,801,243  7/1957  Hanslick et al. ................. 548/346 X

OTHER PUBLICATIONS

*Chemical Abstracts,* 91:158099c (1979) [Ger. 2,820,794, 5/23/79].

Primary Examiner—Richard A. Schwartz
Attorney, Agent, or Firm—Ladas & Parry

[57] ABSTRACT

Novel salts of the formula

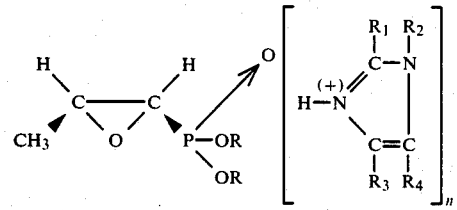

are disclosed wherein n is 1 or 2; both OR groups are $O^-$ when n is 2, or one is $O^-$ and one is OH when n is 1; and $R_1$, $R_2$, $R_3$, and $R_4$ independently represent hydrogen, alkyl, aryl, amino-alkyl, hydroxy-alkyl, or hydroxy-alkyl-amino. These salts are useful in treatment of microbial infecting in mammals, and use of the salts in composition for oral and parenteral administration is also disclosed.

5 Claims, No Drawings

ANTIMICROBIAL SALT OF FOSFOMYCIN WITH IMIDAZOLE

This invention relates to new salts of the antibiotic fosfomycin, chemically designated as (−)(cis-1,2-epoxy-propyl)phosphonic acid. The new salts subject of this invention are those formed with imidazole and derivatives thereof, of general formula I:

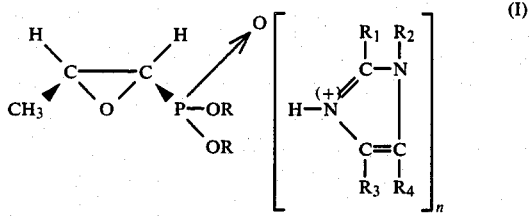

where n may be 1 or 2 and the OR groups are both $O^-$ when n is 2, and one of them is $O^-$ and the other OH when n is 1; $R_1$, $R_2$, $R_3$ and $R_4$, the same or different, represent hydrogen, alkyl, aryl, amino-alkyl, hydroxy-alkyl, and hydroxy-alkylamino groups.

Fosfomycin is an antibiotic discovered in Spain in 1966, which is described in the Merck Index, 9th edition, 1976, No. 4110, page 547, isolated originally from fermentation broths of a strain of *Streptomyces fradiae* obtained from a soil sample collected in Jávea, Alicante, Spain.

Fosfomycin can form mono-salts or di-salts, which are active against Gram-positive and Gram-negative bacteria, and therapeutically useful in the treatment of infections caused thereby. Its antibiotic spectrum comprises the following bacterial species:

| AEROBES | |
|---|---|
| *Staphylococcus aureus* | *Klebsiella sp.* |
| *Streptococcus pyogenes* | *Enterobacter sp.* |
| *Streptococcus pneumoniae* | *Serratia marcescens* |
| *Streptococcus faecalis* | *Pseudomonas aeruginosa* |
| *Neisseria meningitidis* | *Salmonella sp.* |
| *Neisseria gonorrhoeae* | *Shigella sp.* |
| *Haemophilus influenzae* | *Campylobacter fetus jejuni* |
| *Legionella pneumophila* | *Yersinia enterocolitica* |
| *Escherichia coli* | *Acinetobacter calcoaceticus* |
| Indole (−) *Proteus sp.* | *Vibrio cholerae* |
| Indole (+) *Proteus sp.* | *Aeromonas sp.* |
| ANAEROBES | |
| *Peptococcus sp.* | *Fusobacterium sp.* |
| *Peptostreptococcus sp.* | *Clostridium sp.* |

The salts of alkaline metals and alkaline earth metals, such as mono- and di-salts of sodium, potassium, calcium, magnesium, etc., have been known for a long time. Also known are salts formed with amines, such as α-phenethylamine, quinine, lysine, procaine, etc., which can be mono- or di-salts.

The salts of fosfomycin currently used in antibiotherapy are calcium salt for oral administration and sodium salt for parenteral administration (intramuscular and intravenous).

The imidazole salts of fosfomycin display advantages over those used at present, as can be seen from tests carried out on human beings where, by oral administration, the imidazole salts show a significantly higher bioavailability than the calcium and sodium salts. The plasma concentration obtained in crossed tests with the calcium salt and the mono-imidazole salt, at a single oral dose of 1 g, were as follows:

| PLASMA CONCENTRATIONS (μg/ml)* | | |
|---|---|---|
| Time (h) | Calcium fosfomycin | Mono-imidazole fosfomycin |
| 0.5 | — | 2.50 ± 1.50 |
| 1 | 0.90 ± 0.94 | 3.91 ± 1.03 |
| 2 | 3.38 ± 1.44 | 5.71 ± 1.26 |
| 3 | 3.03 ± 1.23 | 4.41 ± 0.78 |
| 4 | 1.95 ± 0.68 | 2.84 ± 0.67 |
| 6 | 0.88 ± 0.48 | 1.64 ± 1.45 |
| 8 | <0.40 | 1.06 ± 0.82 |

*($\bar{x}$ ± tds) (P ≦ 0.05) Average of 6 individuals. Microbiological assay with *Proteus vulgaris* ATCC 21100.

The following table shows the test results, the meaning of the abbreviations being as follows:

AUC=area under the curve resulting from plotting in ordinates the concentration (in μg/ml) of the drug in plasma versus the time (in hours) represented on the abscissae axis.

Ke=elimination constant ($hour^{-1}$).

t1/2=half-life of the drug. This parameter represents the time elapsed until the plasma concentration drops to half.

U∞ =Total amount excreted in the urine (mg).

As can be seen from the data in the table, the bioavailability of the mono-imidazole salt of fosfomycin is 100% higher than that of the calcium salt.

| | (μg/ml)h AUC | ($h^{-1}$) Ke | (h) t½ | ($h^{-1}$) U∞ |
|---|---|---|---|---|
| Calcium fosfomycin | 13.78 | 0.3918 | 1.89 | 225.36 |
| Imidazole fosfomycin | 26.32 | 0.2971 | 2.57 | 363.53 |

In parenteral administration, sodium fosfomycin gives very alkaline aqueous solutions, thus requiring the use of acids to achieve a physiological pH, whereas this in turn increases the tonicity of the solution, and therefore results in painful intramuscular administration, with the additional limitation due to the high sodium content.

The imidazole salts improve or avoid all the side effects of the sodium salt, as the pH of the solutions of the former is closer to the physiological pH and therefore the use of neutralizing acids is not required. Moreover, imidazole potentiates the action of local anesthetics, with the result that the intramuscular administration of the imidazole salt is hardly painful, and besides it eliminates the sodium problem. Slightly superior bioavailability in intramuscular administration is also obtained.

The imidazole salts of fosfomycin of formula I are prepared with [(−)-cis-1,2-epoxypropyl]phosphonic acid, obtained from mono-[(+)-α-phenethylammonium-[(−)cis-1,2-epoxypropyl]phosphonate monohydrate and an ion-exchange resin in a suitable alcohol, such as methanol, ethanol, n-propanol, isopropanol, butanol, etc., or in a mixture thereof, subsequently reacting with imidazole or derivatives thereof of general formula II:

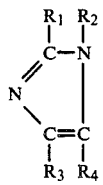

(II)

where $R_1$, $R_2$, $R_3$ and $R_4$ are as defined previously.

The fosfomycin (acid form) is prepared "in situ" from the salt with phenethylamine due to the instability of said free acid form.

The following example is illustrative of the process subject of the invention and should not be considered to be limitative.

EXAMPLE

Preparation of mono(imidazole)-[(−)-cis-1,2-epoxy-propyl]phosphonate salt (mono-imidazole fosfomycin).

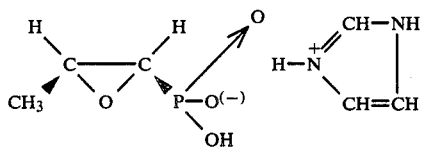

Formula I: $R_1$, $R_2$, $R_3$, $R_4$ = H
$n = 1$, one R = H

Prepare a solution of 20 g of mono(+)-α-phenethylamine salt of fosfomycin in methanol. This solution is treated with 200 g of ion-exchange resin under strong stirring at a temperature comprised between −10° C. and 20° C., preferably at low temperatures due to the instability of the acid, and is filtrated on a porous plate in a flask containing 5.4 g of imidazole. Wash the resin with methanol. Place the flask in an ice bath and stir for 30 minutes. Concentrate under reduced pressure, precipitate with acetone and filtrate.

Thereby obtained is a precipitate or wet cake, which is dried at 50° C. for 8 hours.

About 13 g of mono-(imidazole)-[(−)-cis-1,2-epoxy-propyl]phosphonate are obtained, being characterized by IR in KBr pressed discs, by RMN in deutered water and by other parameters as detailed below:

| | | RMN | |
|---|---|---|---|
| (ppm) | Multiplicity | Integration No. of protons | K coupling J/Hz |
| 1.38 | d, d | 3 | 5.7, 0.75 |
| 2.85 | d, d | 1 | 5.4, 22.7 |
| 3.21 | m | 1 | 5.7, 5.4 |
| 7.37 | | 2 | |
| 8.55 | | 1 | |

IR SPECTRUM:
The IR spectrum displays characteristics bands at 1600, 1410, 1130, 1000, 920 and 800 cm$^{-1}$.

| Melting point | 105–105° C. | | |
|---|---|---|---|
| pH (5% solution) | 5.8 | | |
| Optical rotation | $(\alpha)_{589}^{20}$ (5%, water), −4.4° | | |
| Elemental analysis: | % C | % H | % N |
| Theoretical | 34.96 | 5.34 | 13.58 |

| -continued | | | |
|---|---|---|---|
| Result | 34.62 | 5.38 | 13.60 |

Antibacterial activity:
Against Proteus vulgaris ATCC 21100, equivalent to 630 μg of free fosfomycin acid/mg.

| PHARMACEUTICAL FORMS | | |
|---|---|---|
| ORAL ROUTE | | |
| CAPSULES (250 mg) | | |
| Fosfomycin-Imidazole (mono-salt) | 250 mg | (free fosfomycin acid equivalent) |
| Magnesium stearate | 4 mg | |
| Lactose up to | 450 mg | |
| SACHETS (500 mg) | | |
| Fosfomycin-Imidazole (mono-salt) | 500 mg | (free fosfomycin acid equivalent) |
| 6-fruit flavour | 150 mg | |
| Sucrose up to | 3500 mg | |
| SACHETS (1000 mg) | | |
| Fosfomycin-Imidazole (mono-salt) | 1000 mg | (free fosfomycin acid equivalent) |
| 6-fruit flavour | 250 mg | |
| Sucrose up to | 4000 mg | |
| PARENTERAL ROUTE | | |
| INJECTABLE (intramuscular) 1 g | | |
| Each vial contains: | | |
| Fosfomycin-Imidazole (mono-salt) | 1000 mg | (free fosfomycin acid equivalent) |
| Each ampoule contains: | | |
| Lidocaine ClH | 25 mg | |
| Water for injection up to | 4 ml | |
| INJECTABLE (intravenous) 1 g | | |
| Each vial contains: | | |
| Fosfomycin-Imidazole (mono-salt) | 1000 mg | (free fosfomycin acid equivalent) |
| INJECTABLE (intravenous) 4 g | | |
| Each vial contains: | | |
| Fosfomycin-Imidazole (mono-salt) | 4000 mg | (free fosfomycin acid equivalent) |

We claim:
1. A salt of the formula

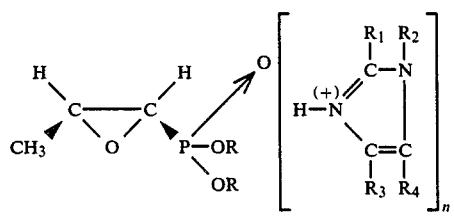

wherein n is 1 and one of the two OR groups is O$^-$ and the other one is OH; and $R_1$, $R_2$, $R_3$ and $R_4$ independently represent hydrogen.

2. A composition for treatment of microbial infections in mammals, comprising as an active ingredient an antimicrobially effective amount of a salt of the formula

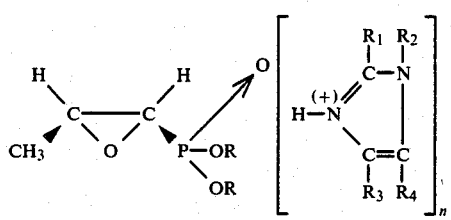

wherein n is 1 and one of the two OR groups is O⁻ and the other one is OH; and $R_1$, $R_2$, $R_3$ and $R_4$ independently represent hydrogen together with a pharmaceutically acceptable carrier or excipient.

3. A composition according to claim 2 for oral administration comprising 250–1000 mg of active ingredient per unit dose.

4. A composition according to claim 2 for parenteral administration comprising 1 g–4 g of active ingredient per unit dose.

5. A method for treating microbial infections in mammals, including human beings, comprising administering thereto an antimicrobially effective amount of a salt of the formula

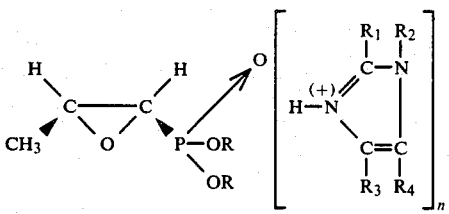

wherein n is 1 and one of the two OR groups is O⁻ and the other one is OH and $R_1$, $R_2$, $R_3$ and $R_4$ independently represent hydrogen.

* * * * *

UNITED STATES PATENT AND TRADEMARK OFFICE
CERTIFICATE OF CORRECTION

PATENT NO. : 4 675 315
DATED : June 23, 1987
INVENTOR(S) : Austin PRIETO PRIETO

It is certified that error appears in the above-identified patent and that said Letters Patent is hereby corrected as shown below:

Title Page, Column 1, delete the inventors names

"Agustin P. Prieto and Arturo T. Higom" and replace therefor -- Agustin PRIETO PRIETO Arturo TORREGROSA HIGOM and Maria del Pilar CABELLO MATA --

Title Page, Column 1, delete the assignee name and replace therefor -- COMPANIA ESPANOLA DE LA PENICILINA Y

ANTIBIOTICOS, S.A. --

Signed and Sealed this

Third Day of January, 1989

*Attest:*

DONALD J. QUIGG

*Attesting Officer*      *Commissioner of Patents and Trademarks*